United States Patent
Melander et al.

(10) Patent No.: US 10,335,536 B2
(45) Date of Patent: Jul. 2, 2019

(54) PEN-TYPE DRUG INJECTION DEVICE HAVING MULTIPLE-USE NEEDLE MODULE WITH NEEDLE CLEANING RESERVOIR

(71) Applicant: Novo Nordisk A/S, Bagsvaerd (DK)

(72) Inventors: Matias Melander, Copenhagen (DK); Christian Hoejris Nielsen, Copenhagen (DK); Mie Haraldsted, Helsingoer (DK)

(73) Assignee: Novo Nordisk A/S, Bagsvaerd (DK)

(*) Notice: Subject to any disclaimer, the term of this patent is extended or adjusted under 35 U.S.C. 154(b) by 188 days.

(21) Appl. No.: 15/310,008

(22) PCT Filed: May 8, 2015

(86) PCT No.: PCT/EP2015/060239
§ 371 (c)(1),
(2) Date: Nov. 9, 2016

(87) PCT Pub. No.: WO2015/173151
PCT Pub. Date: Nov. 19, 2015

(65) Prior Publication Data
US 2017/0136173 A1 May 18, 2017

(30) Foreign Application Priority Data
May 13, 2014 (EP) .................................. 14168126

(51) Int. Cl.
*A61M 5/00* (2006.01)
*A61M 5/32* (2006.01)
(Continued)

(52) U.S. Cl.
CPC ............ *A61M 5/001* (2013.01); *A61M 5/326* (2013.01); *A61M 5/3245* (2013.01);
(Continued)

(58) Field of Classification Search
CPC .... A61M 5/001; A61M 5/326; A61M 5/3245; A61M 5/3293; A61M 2209/10;
(Continued)

(56) References Cited

U.S. PATENT DOCUMENTS 3,354,881 A 11/1967 Bloch
4,416,663 A 11/1983 Hall
(Continued)

FOREIGN PATENT DOCUMENTS

DE 19845618 A1 4/2000
EP 182682 A1 5/1986
(Continued)

*Primary Examiner* — Bhisma Mehta
*Assistant Examiner* — Hamza A Darb
(74) *Attorney, Agent, or Firm* — Wesley Nicolas

(57) ABSTRACT

Disclosed is a medical injection device (1) comprising a needle assembly (20) having a cannula (21) and a telescopic shield (30) for covering the distal tip (23) in a no use situation. The telescopic shield further carries a cleaning reservoir (40) for cleaning the needle cannula between two subsequent injections. The cleaning reservoir is provided with an opening (43) connecting to an overflow reservoir (51/55) such that the cleaning liquid contained in the cleaning reservoir can retract and expand upon temperature changes and does not enter the needle lumen instead. In one example, the overflow reservoir is formed as a channel (51).

12 Claims, 3 Drawing Sheets

(52) U.S. Cl.
CPC ... *A61M 5/3293* (2013.01); *A61M 2005/3267* (2013.01); *A61M 2209/10* (2013.01)

(58) Field of Classification Search
CPC ........ A61M 2005/3267; A61M 5/3243; A61M 2205/0205; A61L 2202/24; A61J 1/1443
See application file for complete search history.

(56) References Cited

U.S. PATENT DOCUMENTS

| | | | | |
|---|---|---|---|---|
| 4,666,436 A * | 5/1987 | McDonald | ........... | A01K 11/002 604/198 |
| 4,769,026 A * | 9/1988 | Strung | ................. | A61M 5/001 604/263 |
| 5,147,311 A * | 9/1992 | Pickhard | ............... | A61M 5/148 604/131 |
| 5,894,015 A | 4/1999 | Rechtin | | |
| 2016/0001014 A1* | 1/2016 | Eilertsen | ............... | A61M 5/326 604/198 |

FOREIGN PATENT DOCUMENTS

| WO | 2014029018 A1 | 2/2014 |
|---|---|---|
| WO | 2014064100 A1 | 5/2014 |
| WO | 2015062845 A1 | 5/2015 |

* cited by examiner

PEN-TYPE DRUG INJECTION DEVICE HAVING MULTIPLE-USE NEEDLE MODULE WITH NEEDLE CLEANING RESERVOIR

CROSS-REFERENCE TO RELATED APPLICATIONS

This application is a 35 U.S.C. § 371 National Stage application of International Application PCT/EP2015/060239 (published as WO 2015/173151), filed May 8, 2015, which claims priority to European Patent Application 14168126.2, filed May 13, 2014; the contents of which are incorporated herein by reference.

THE TECHNICAL FIELD OF THE INVENTION

The invention relates to a medical injection device having a shielded needle cannula. The invention especially refers to such an injection device wherein the shielded needle cannula is provided for repeated use and the distal tip of the needle cannula penetrating into the skin of the user during injection is cleaned between subsequent injections.

DESCRIPTION OF RELATED ART

Injection devices wherein the tip of the needle cannula is maintained in a cleaning solvent between subsequent injections are disclosed in U.S. Pat. Nos. 3,354,881, 4,416,663, 4,666,436, WO 2014/064100 and in EP 182,682. As can be seen from these prior art injection devices, the cleaning chamber is usually carried distally on a retractable shield covering the tip of the needle cannula between subsequent injections.

Further WO 2014/064100 discloses a pre-filled disposable injection device which has a telescopically shield covering the distal tip of the needle cannula between subsequent injections. This telescopically shield is urged into a distal covering position by a spring. Further, in one embodiment, the shield is provided with a hollow chamber containing a liquid solvent such as a chemical disinfectant or biocide which cleans the tip of the needle cannula between subsequent injections. Examples on such cleaning solvents are provided in WO 2014/029018.

WO 2015/062845 disclose the possibility of using the liquid medical drug contained inside the cartridge as a cleaning solvent. This requires that the liquid drug contains a preservative which is often the case. In one embodiment the cleaning reservoir is filled with liquid drug directly from the cartridge of the injection device by the user when initiating first use. However, the cleaning reservoir could also be filled by the manufacture.

Between subsequent injections, the distal tip of the needle cannula is maintained inside the cleaning reservoir and the proximal part is maintained inside the cartridge. The liquid system thus comprises the inside of the cleaning reservoir, the hollow lumen of the needle cannula and the hollow interior of the cartridge.

Since injection devices usually are kept in a refrigerator when not in use to maintain the life-time of the liquid drug, the liquid drug in the liquid system is exposed to a relatively high temperature change when moved from the refrigerator to room temperature and vice versa. In some areas of the world the change could be from approximately 5 degrees Celsius inside the refrigerator and up to 40 to 45 degrees Celsius outside the refrigerator. This temperature change makes the liquid drug contained in the liquid system expand and retract.

DESCRIPTION OF THE INVENTION

It is thus an object of the present invention to provide an injection device with a cleaning reservoir which can obtain both expansion and retraction of the liquid cleaning solvent in the liquid system.

The invention is defined in claim 1. Accordingly in one aspect the present invention relates to a medical injection device by which a user can apportion set doses of a liquid drug.

The injection device comprises:

A housing which supports a cartridge containing the liquid drug.

A needle cannula having a distal part with a distal tip and an opposite proximal part. A longitudinal lumen connects the ends of the needle cannula. The needle cannula is mounted such in relation to the housing that the distal part extend in a distal direction to penetrate into the user and the proximal part extend in a proximal direction and penetrates into the cartridge whereby a liquid pass-way can be established between the interior of the cartridge and the body of the user during injection.

A telescopically movable shield which is telescopically movable in relation to the housing and urged in the distal direction by a spring means operable between the telescopically movable shield and the housing, and wherein the telescopically movable shield carries a first cleaning reservoir containing a liquid cleaning solvent for cleaning at least the distal tip of the needle cannula between subsequent injections, The first cleaning reservoir is distally closed by a distal seal (e.g. a septum) and proximally closed by a proximal seal (e.g. a septum). These two seals are longitudinal spaced from each other to define a volume containing the cleaning solvent. The first cleaning reservoir is further provided with an opening which connects the first cleaning reservoir with a second overflow reservoir.

The distal seal and the proximal seal fit tightly to the needle cannula to prevent the liquid cleaning solvent from escaping along the side of the needle cannula. Either one or both of the distal seal and the proximal seal can be formed as septums. The thus distal septum and the proximal septum are together with the septum of the cartridge supposed to be penetrated by the needle cannula. The septums are henceforth made from a material which accommodates such penetration.

The feature that the spring means are operable incorporated between the telescopically movable shield and the housing, does not necessarily mean that the spring means are physically located directly between the telescopically movable shield and the housing. It merely means that the function that the spring means provides operates the telescopically movable shield relatively to the housing. In one example of the invention the spring means is a compression spring encompassed between an element which at least during use is connected to the housing and a second part being the telescopically movable shield or a part connected to the telescopically movable shield.

Due to the opening between the first cleaning reservoir and the second overflow reservoir, It is possible when the cleaning solvent in the liquid system expands to flow through this opening and into the overflow reservoir and vice versa. The opening and its connection to the second overflow reservoir thereby accommodate a volume expansion of the liquid cleaning solvent contained in the first cleaning reservoir.

The opening usually has a well-defined size which is chosen to accommodate the wanted flow from the first cleaning reservoir and to the second overflow reservoir and back again.

The first cleaning reservoir and the second overflow reservoir can either form a closed system or the second overflow reservoir can be open to the atmosphere.

In one aspect of the invention, an amount of liquid cleaning solvent is always present in the second overflow reservoir. This amount is preferably determined such that when the liquid cleaning solvent retracts during cooling there is always sufficient liquid cleaning solvent present in the system to maintain an amount inside the second overflow reservoir. This strongly reduces the possibility for germs and bacteria to enter into the first cleaning reservoir.

The second overflow reservoir can have any shape and is preferably carried by the telescopically movable shield. In this way the first cleaning reservoir and the second overflow reservoir can be provided e.g. side-by-side only separated by a wall having the opening. When both reservoirs are carried by the shield, the entire shield can be manufactured in a suitable polymeric material by a well-known moulding process. The two reservoirs can also be made as individual parts and connected to the shield.

The needle cannula which forms a liquid channel between the interior of the cartridge and the inside of the first cleaning chamber can in one example be permanently connected to the housing of the injection device such that the same needle cannula is used multiple times and preferably until the entire content of the injection device has been used. However, alternatively the needle cannula can form part of a needle assembly which is attached to the injection device by suitable attachment means such as a thread or bayonet connection. The needle assembly is thus mounted onto a prefilled injection device when taking the prefilled injection device into its first use and the coupling between the needle assembly and the injection device is preferably constructed such that the needle assembly cannot be removed once it is mounted.

However, no matter if the needle cannula is permanently connected to the housing or attachable secured to the housing, the same needle cannula is intended to be used throughout the lifetime of the prefilled injection device.

The second overflow reservoir is preferably formed as a channel connected to the first cleaning reservoir through the opening. The channel preferably has a tube-like configuration. The channel can be formed as a longitudinal channel e.g. a longitudinal tubular channel, but is preferably formed as a curved channel and most preferably as a helical channel which in one example can be helically wounded around the first cleaning reservoir.

In one example, the helical channel can be moulded as an open spiral in one part which is thereafter connected to a different part which in one example could also carry the first cleaning reservoir. The different part attached to the first part henceforth makes up the wall that closes and seals the spiral to make up a channel.

The first cleaning reservoir is in a situation of use filled with the cleaning solvent. Further it is beneficial if the first cleaning reservoir is in fact overfilled such that a predetermined amount of the cleaning solvent has flown into the second overflow reservoir. This is especially beneficial when the second overflow reservoir is shaped as a channel such that an amount of the cleaning solvent can be present in the channel thus preventing dirt, germs and bacteria from entering into through the second overflow reservoir and into the first cleaning reservoir. The level to which the channel should be filled should preferably be calculated such that there is always liquid cleaning solvent inside the channel when the liquid drug retracts during cooling, and the channel should have a sufficient volume to allow expansion of the liquid drug in the first cleaning reservoir without the cleaning solvent escaping from the end of the channel.

In one aspect, the channel terminates to the atmosphere preferably through a reduced diameter in order to prevent dirt, germs and bacteria from entering into the channel or at least to reduce the admissibility of dirt, germs and bacteria.

A further way to prevent entry of dirt, germs and bacteria is to provide the outer end of the channel with a filter e.g. a biological filter impermeable to germs and bacteria. In another example the outer end of the channel is simply closed. Alternatively, the channel can be connected to a balloon. As an alternative to a balloon the termination of the channel can connect to a bellows or an accordion or the like.

The liquid cleaning solvent inside the first cleaning chamber can be any suitable solvent which reduces the presence of germs or bacteria on the distal tip of the needle cannula. In one example, the cleaning solvent used is identical to the preservative used to maintain the life-time of the liquid drug inside the cartridge. Many liquid drug formulations comprise a preservative which hinders bacterial growth in the liquid drug. This preservative could as an example be phenol or metacresol or a combination of both. In a preferred example, the liquid preservative containing drug from the cartridge is also used as the cleaning solvent.

When using the same liquid preservative containing drug as the cleaning solvent, the first cleaning reservoir is either filled by the manufacture or by the user when taking the injection device into first use. When filled by the user it can be done either manually or automatically as a response to the user performing certain steps.

DEFINITIONS

An "injection pen" is typically an injection apparatus having an oblong or elongated shape somewhat like a pen for writing. Although such pens usually have a tubular cross-section, they could easily have a different cross-section such as triangular, rectangular or square or any variation around these geometries.

The term "Needle Cannula" is used to describe the actual conduit performing the penetration of the skin during injection. A needle cannula is usually made from a metallic material such as e.g. stainless steel and connected to a hub to form a complete injection needle also often referred to as a "needle assembly". A needle cannula could however also be made from a polymeric material or a glass material. The hub also carries the connecting means for connecting the needle assembly to an injection apparatus and is usually moulded from a suitable thermoplastic material. The "connection means" could as examples be a luer coupling, a bayonet coupling, a threaded connection or any combination thereof e.g. a combination as described in EP 1,536,854. Needle assemblies specially designed for pen injections system are defined in ISO standard No. 11608, part 2, and are often referred to as "pen needles". Pen needles usually have a front-end for penetrating into the user and a back-end for penetrating into the cartridge containing the drug.

As used herein, the term "drug" is meant to encompass any drug-containing flowable medicine capable of being passed through a delivery means such as a hollow needle in a controlled manner, such as a liquid, solution, gel or fine suspension. Representative drugs includes pharmaceuticals such as peptides, proteins (e.g. insulin, insulin analogues and C-peptide), and hormones, biologically derived or active agents, hormonal and gene based agents, nutritional formulas and other substances in both solid (dispensed) or liquid form.

"Cartridge" is the term used to describe the container actually containing the drug. Cartridges are usually made from glass but could also be moulded from any suitable polymer. A cartridge or ampoule is preferably sealed at one end by a pierceable membrane referred to as the "septum" which can be pierced e.g. by the non-patient end of a needle cannula. Such septum is usually self-sealing which means that the opening created during penetration seals automatically by the inherent resiliency once the needle cannula is removed from the septum. The opposite end is typically closed by a plunger or piston made from rubber or a suitable polymer. The plunger or piston can be slidable moved inside the cartridge. The space between the pierceable membrane and the movable plunger holds the drug which is pressed out as the plunger decreased the volume of the space holding the drug. However, any kind of container—rigid or flexible—can be used to contain the drug.

Since a cartridge usually has a narrower distal neck portion into which the plunger cannot be moved not all of the liquid drug contained inside the cartridge can actually be expelled. The term "initial quantum" or "substantially used" therefore refers to the injectable content contained in the cartridge and thus not necessarily to the entire content.

By the term "Pre-filled" injection device is meant an injection device in which the cartridge containing the liquid drug is permanently embedded in the injection device such that it cannot be removed without permanent destruction of the injection device. Once the pre-filled amount of liquid drug in the cartridge is used, the user normally discards the entire injection device. This is in opposition to a "Durable" injection device in which the user can himself change the cartridge containing the liquid drug whenever it is empty. Pre-filled injection devices are usually sold in packages containing more than one injection device whereas durable injection devices are usually sold one at a time. When using pre-filled injection devices an average user might require as many as 50 to 100 injection devices per year whereas when using durable injection devices one single injection device could last for several years, however, the average user would require 50 to 100 new cartridges per year.

Using the term "Automatic" in conjunction with injection device means that, the injection device is able to perform the injection without the user of the injection device delivering the force needed to expel the drug during dosing. The force is typically delivered—automatically—by an electric motor or by a spring drive. The spring for the spring drive is usually strained by the user during dose setting, however, such springs are usually prestrained in order to avoid problems of delivering very small doses. Alternatively, the spring can be fully preloaded by the manufacturer with a preload sufficient to empty the entire drug cartridge though a number of doses. Typically, the user activates a latch mechanism e.g. in the form of a button on, e.g. on the proximal end, of the injection device to release—fully or partially—the force accumulated in the spring when carrying out the injection.

The term "Permanently connected" or "permanently embedded" as used in this description is intended to mean that the parts, which in this application is embodied as a cartridge permanently embedded in the housing, requires the use of tools in order to be separated and should the parts be separated it would permanently damage at least one of the parts.

All references, including publications, patent applications, and patents, cited herein are incorporated by reference in their entirety and to the same extent as if each reference were individually and specifically indicated to be incorporated by reference and were set forth in its entirety herein.

All headings and sub-headings are used herein for convenience only and should not be constructed as limiting the invention in any way.

The use of any and all examples, or exemplary language (e.g. such as) provided herein, is intended merely to better illuminate the invention and does not pose a limitation on the scope of the invention unless otherwise claimed. No language in the specification should be construed as indicating any non-claimed element as essential to the practice of the invention.

The citation and incorporation of patent documents herein is done for convenience only and does not reflect any view of the validity, patentability, and/or enforceability of such patent documents.

This invention includes all modifications and equivalents of the subject matter recited in the claims appended hereto as permitted by applicable law.

BRIEF DESCRIPTION OF THE DRAWINGS

The invention will be explained more fully below in connection with a preferred embodiment and with reference to the drawings in which.

The figures are schematic and simplified for clarity, and they just show details, which are essential to the understanding of the invention, while other details are left out. Throughout, the same reference numerals are used for identical or corresponding parts.

DETAILED DESCRIPTION OF EMBODIMENT

When in the following terms as "upper" and "lower", "right" and "left", "horizontal" and "vertical", "clockwise" and "counter clockwise" or similar relative expressions are used, these only refer to the appended figures and not to an actual situation of use. The shown figures are schematic representations for which reason the configuration of the different structures as well as there relative dimensions are intended to serve illustrative purposes only.

In that context it may be convenient to define that the term "distal end" in the appended figure is meant to refer to the end of the injection device which points towards the skin of the user upon injection and which carries the injection needle whereas the term "proximal end" is meant to refer to the opposite end of the injection device which usually carrying the dose setting button. "Distal" and "proximal" is meant to be along an axial orientation extending along the longitudinal axis of the injection device.

Figure 1:
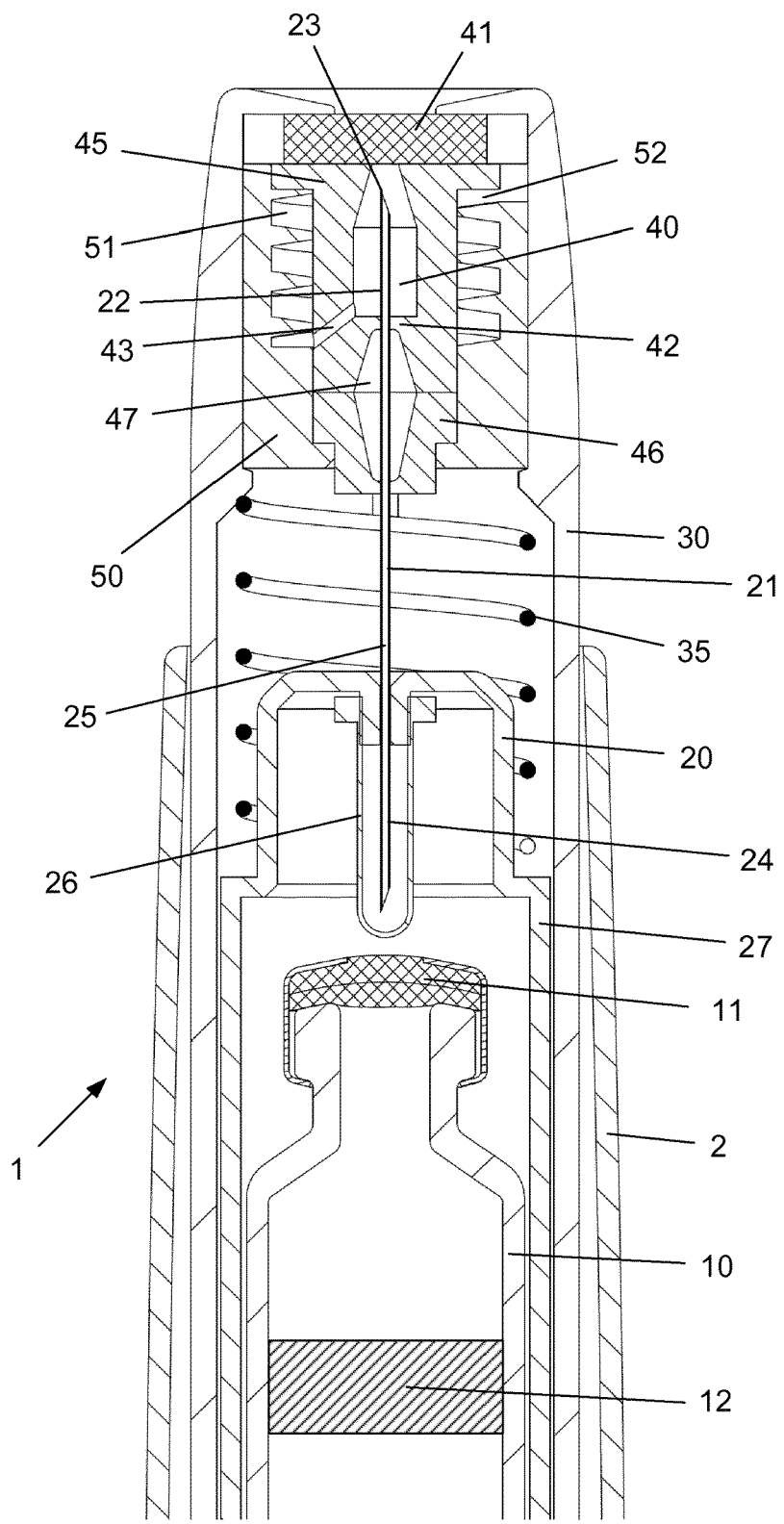
FIG. 1 show a cross-sectional view of the distal end of a pen shaped injection device according to a first example of the invention.

FIG. 1 discloses the distal end of a pen shaped injection device 1. The liquid drug is contained in a cartridge 10 which distally is closed by a pierceable septum 11 and proximally provided with a movable plunger 12 which is moved forward by a non-shown injection mechanism.

A needle assembly 20 is provided which in the depictured embodiment is an integral part of a needle holder 27 which can telescope in relation to the cartridge 10. This needle assembly 20 comprises a needle cannula 21 defining a lumen 25 and having a distal part 22 with a distal tip 23 for penetrating the skin of user during injection. The opposite proximal part 24 is ready to be pierced through the septum 11 and into the interior of the cartridge 10 such that the liquid drug can flow from the cartridge 10 and into the user during injection. When not pierced through the septum 11, the proximal part 24 is covered by a rubber bag 26 and thereby maintained sterile.

Further, a telescopically movable shield 30 is provided which covers the distal part 22 of the needle cannula 21 in a non-use situation as depicted on FIG. 1. The shield 30 is slidable mounted in the housing 2 of the injection device 1.

The telescopically movable shield 30 is urged into its extended position by a spring 35 which is encompassed between the needle holder 27 and the shield 30. When the distal end of the shield 30 is pressed against the skin of a user, the shield 30 moves proximally as the spring 35 compresses. Once the injection is over and the distal end of the shield 30 is removed from the skin of the user, the spring 35 urges the shield 30 in the distal direction. The injection can either be manually performed by the user pushing a non-shown injection button back into the housing 2, or it can be done automatically e.g. by an electric motor or by a spring driven motor. If the injection is done automatically the motor (electric or spring) can be released to inject by the proximal movement of the shield 30. This is often referred to as shield-triggered injection.

In one aspect, the needle assembly 20 and thus the needle cannula 21 is permanently attached to the injection device 1 and the same needle cannula 21 is used for multiple injections. Such injection devices 1 are often pre-filled with a limited amount of liquid drug, and the needle cannula 21 is used for the life-time of the prefilled injection device 1 thus the user does not have to change the needle assembly 20 during the life time of the injection device 1.

In an example, the injection device 1 can be prefilled by the manufacture with e.g. 300 International Units (IU) of a liquid insulin solution, which is then all injected through the same needle cannula 21 in a multiple number of injections where after the injection device 1 and the needle cannula 21 are discarded together.

In order to keep at least the distal tip 23 of the needle cannula 21 clean, a cleaning reservoir 40 is provided in the shield 30, which cleaning reservoir 40 is filled with the same liquid drug as contained in the cartridge 10. Since drugs usually contain a preservative, this preservative keeps the distal tip 23 of the needle cannula 21 clean between subsequent injections.

The cleaning reservoir 40 is distally closed by a distal septum 41 and proximally by a proximal septum 42 which are spaced apart in the longitudinal direction to form the cleaning reservoir 40. During injection when the shield 30 is moved proximally, the distal part 23 of the needle cannula 21 penetrates through the distal septum 41.

The reservoir 40 is, as disclosed, formed in a first insert 45, the purpose of which will be explained later. Proximally this first insert 45 abut a second insert 46 such that a second chamber 47 is formed between the first insert 45 and the second insert 46. The purpose of this second chamber 47, which is sterilized before delivery of the injection device 1 to the user, is to maintain the part of the needle cannula 21 next to the distal part 22 in a sterile environment, at least until first use on the injection device 1.

The first insert 45 and the second insert 46 are both carried by an outer insert 50 which is press fitted into the shield 30. The first insert 45, the second insert 46 and the outer insert 50 is all made from a synthetic rubber material. A second reservoir channel 51 is formed in the inner surface of the outer insert 50. This channel 51 is in FIG. 1 depicted as being helical, but can be any shape. The channel 51 is preferably formed in the outer insert 50 and sealed by a surface of the first insert 45. The channel 51 is connected to the reservoir 40 via an opening 43 which is formed in the first insert 45. In the other end, the channel 51 terminates into an outlet 52 as will be explained in the following.

Figure 2:
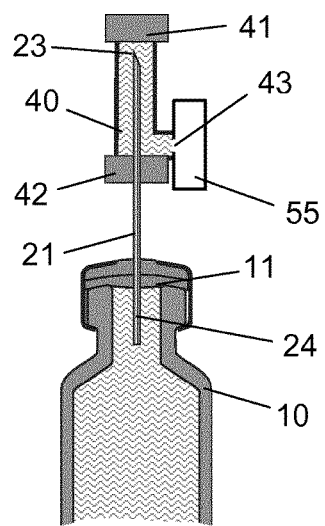
FIG. 2 show a schematic view of the principle of the invention.
Figure 3:
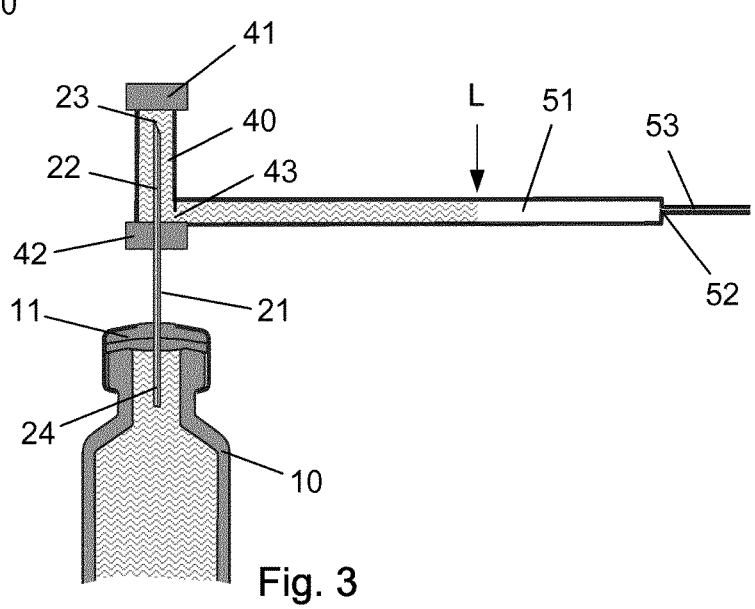
FIG. 3 show a schematic view of the principle of an embodiment of the invention.
Figure 4:
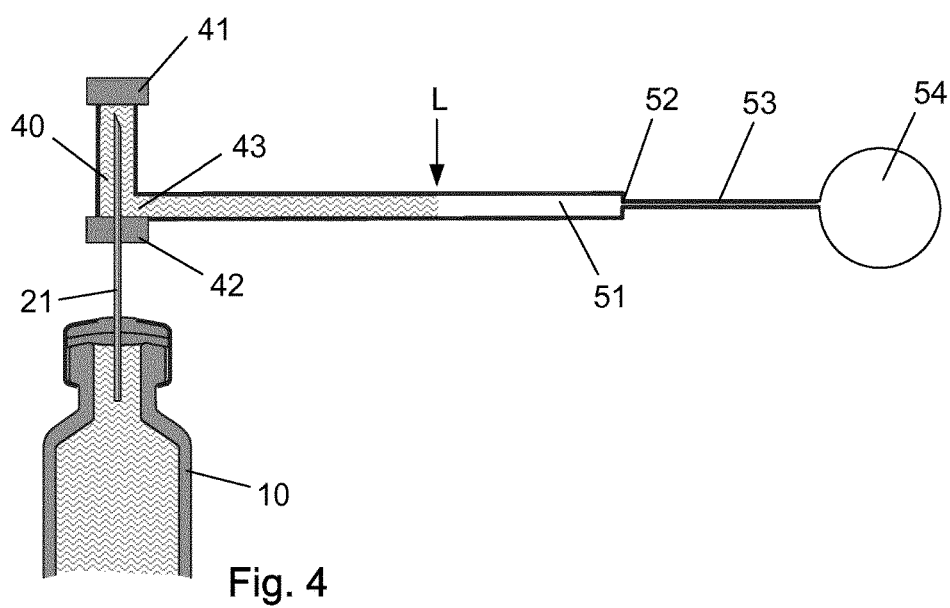
FIG. 4 show a schematic view of the principle of a further embodiment of the invention.

The principle of the invention is disclosed in FIGS. 2 to 4. The proximal part 24 of the needle cannula 21 is here pierced through the septum 11 and into the interior of the cartridge 10 whereas the distal part 22 and especially the distal tip 23 is maintained inserted into the cleaning reservoir 40.

The cleaning reservoir 40 is encompassed between the distal septum 41 and the proximal septum 42 which are longitudinal displaced from each other. The cleaning reservoir 40 is connected to the second overflow reservoir 55 through an opening 43.

In FIG. 1 the second overflow reservoir 55 is formed as a channel 51 whereas in the example in FIG. 2, the overflow reservoir 55 is formed as a rectangular compartment.

When the overflow reservoir 55 is formed as a channel 51 it can be helical as depicted in FIG. 1, however in the principles FIGS. 3 and 4 the overflow reservoir 55 is formed as a channel 51 which is depicted as a straight tube.

When a user takes a new injection device 1 into use, the user fills the cleaning reservoir 40 with liquid drug directly from the cartridge 10 simply by injecting into the cleaning reservoir 40. The filling could also be implemented automatically when the user prepares the injection device 1 for injection. The cleaning reservoir 40 is preferably filed such that the liquid drug flow into the channel 51 to a certain level indicated by "L" in FIGS. 3 and 4.

The liquid drug inside the cleaning reservoir 40 is thus able to both expand and retract as the surrounding temperature changes.

The outlet 52 at the outer end of the channel 51 is in one example open to the atmosphere such that the pressure on the liquid drug inside the cleaning reservoir 40 is that of the surrounding atmosphere. An outer part 53 of the channel 51 bordering the outlet 52 preferably has a narrow diameter as disclosed in FIG. 3 to prevent dirt, germs and bacteria to travel from the surrounding atmosphere and into the cleaning reservoir 40. Alternatively, the opening 52 can be covered by a filter or the like.

In the embodiment disclosed in principle in FIG. 4, the outlet 52 opens into a balloon 54 such that the system is entirely without contact to the surrounding atmosphere. The balloon 54 can either be coupled directly to the channel 51 or via the more narrow outer part 53 as disclosed in FIG. 4. The balloon 54 is however only one example, other configurations of flexible diaphragms can easily be envisaged such as a bellows, an accordion or the like.

Further in FIG. 4, the opening 43 between the cleaning reservoir 40 and the overflow reservoir 55 in form of a channel 51 has the same diameter as the channel 51, whereas in FIG. 3, the diameter of the opening 43 is somewhat reduced in comparison with the diameter of the channel 51.

Figure 5:
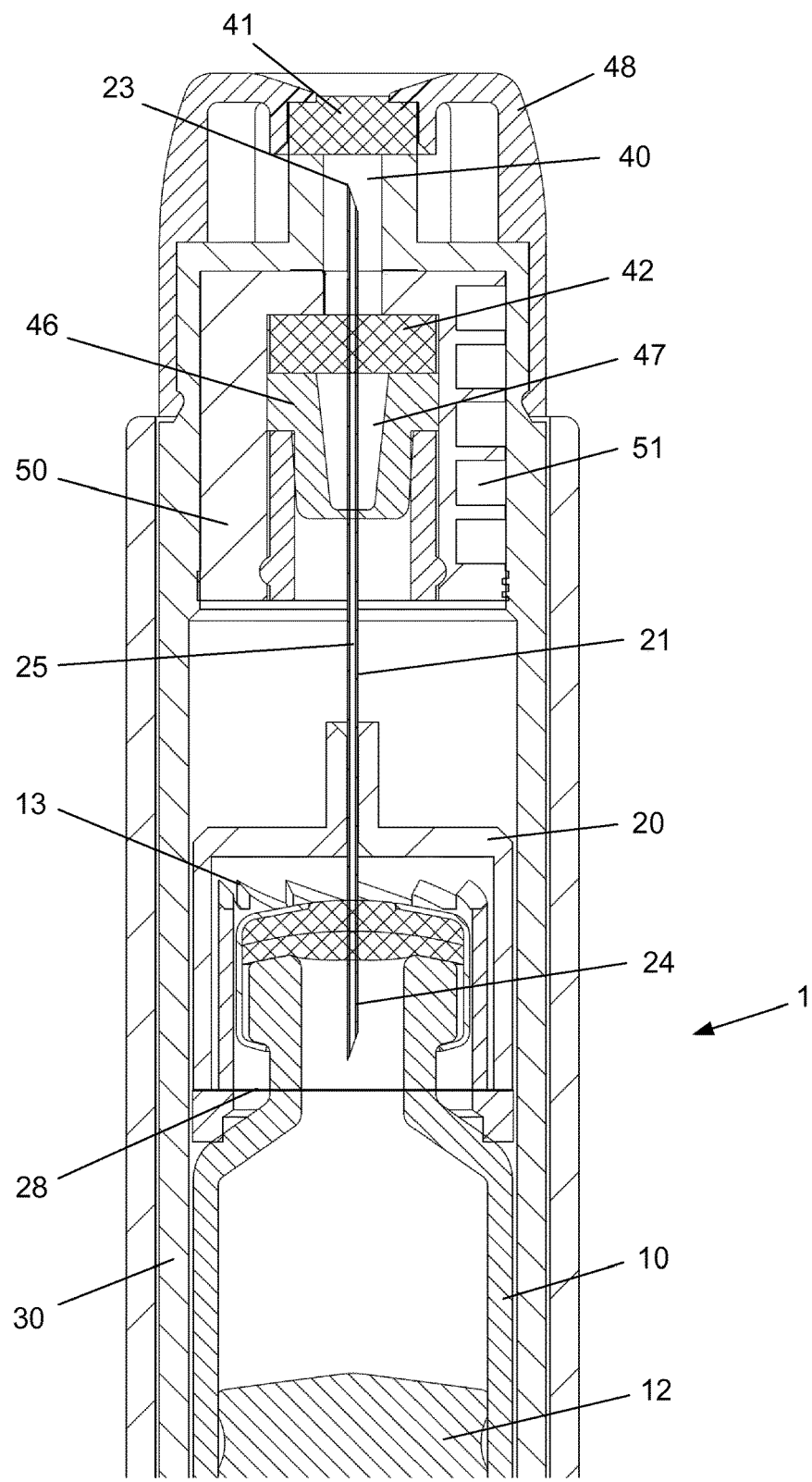
FIG. 5 shows a cross-sectional view of the distal end of a pen shaped injection device according to a second example of the invention.

FIG. 5 depicts yet another embodiment comprising a cartridge 10, a needle assembly 20 and a telescopic shield 30 carrying a cleaning chamber 40.

The interior of the needle assembly 20 is maintained sterile by a barrier 28 which is cut open by a cutter 13 when the needle assembly 20 is moved proximally when initiating injection.

As can be seen in FIG. 5 the configuration of the cleaning chamber 40 is slightly different. Distally the cleaning chamber 40 is bordered by a distal septum 41 and proximally by a proximal septum 42. This proximal septum 42 abuts a second insert 46 which thereby defines a second chamber 47. Distally the distal septum 41 is secured by a front part 48 which clicks to the telescopic shield 30.

Further, a non-shown spring can be encompassed between the shield 30 and the needle assembly 20 to urge the telescopic shield 30 in the distal direction. The needle assembly 20 and the needle cannula 21 is also in this embodiment a permanent part of the injection device 1.

As in the first embodiment, the channel 51 is provided in an outer insert 50. The channel 51 is disclosed as formed as hairpin bends i.e. curved segments, but could also in this embodiment be helical or straight or in fact any desired shape.

For reasons of manufacture, the channel 51 is formed in one element and sealed by a second element as disclosed in FIG. 1 and in FIG. 5.

Some preferred embodiments have been shown in the foregoing, but it should be stressed that the invention is not limited to these, but may be embodied in other ways within the subject matter defined in the following claims.

The invention claimed is:

1. A medical injection device for apportioning set doses of a liquid drug, comprising
- a housing supporting a cartridge containing the liquid drug,
- a needle cannula having a distal part with a distal tip and an opposite proximal part and a longitudinal lumen there between, the needle cannula being mounted relatively to the housing such that the distal part extend in a distal direction and the proximal part extend in a proximal direction and into the cartridge,
- a telescopically movable shield which is telescopically movable in relation to the housing and urged in the distal direction by a spring means operable between the telescopically movable shield and the housing, and wherein the telescopically movable shield carries a first cleaning reservoir containing a liquid cleaning solvent for cleaning at least the distal tip of the needle cannula between subsequent injections,
- wherein the first cleaning reservoir distally is sealed by a distal seal and proximally by a proximal seal longitudinal spaced from each other to define a volume containing the cleaning solvent and wherein the first cleaning reservoir further is provided with an opening connecting the first cleaning reservoir with a second overflow reservoir to accommodate a volume expansion of the liquid cleaning solvent contained in the first cleaning reservoir, and
- wherein a predetermined amount of liquid cleaning solvent is present inside the second overflow reservoir.

2. A medical device according to claim 1, wherein the second overflow reservoir is carried by the telescopically movable shield.

3. A medical device according to claim 1, wherein the needle cannula is permanently mounted to the housing.

4. A medical device according to claim 1, wherein the second overflow reservoir is formed as a channel.

5. A medical device according to claim 4, wherein the channel is curved.

6. A medical device according to claim 5, wherein the channel is helical.

7. A medical device according to claim 4, wherein the cleaning solvent in the second outflow reservoir is filled to a predetermined level (L) inside the channel.

8. A medical device according to claim 4, wherein the channel terminates to the atmosphere via an outlet.

9. A medical device according to claim 4, wherein an outer part of the channel internally has a reduced diameter.

10. A medical device according to claim 4, wherein the channel is provided with a filter.

11. A medical device according to claim 4, wherein the channel is closed.

12. A medical device according to claim 1, wherein the liquid cleaning solvent in the cleaning reservoir is identical with a preservative containing liquid drug contained in the cartridge.

* * * * *